United States Patent [19]

Rosenthal et al.

[11] Patent Number: 4,633,087
[45] Date of Patent: Dec. 30, 1986

[54] NEAR INFRARED APPARATUS FOR MEASUREMENT OF ORGANIC CONSTITUENTS OF MATERIAL

[75] Inventors: Glenn K. Rosenthal, Germantown; Jeffrey D. Stephens; Robert D. Rosenthal, both of Gaithersburg, all of Md.

[73] Assignee: Trebor Industries, Inc., Gaithersburg, Md.

[21] Appl. No.: 726,658

[22] Filed: Apr. 24, 1985

[51] Int. Cl.$^4$ ............................................. G01J 1/00
[52] U.S. Cl. ..................................... 250/341; 250/339
[58] Field of Search ............ 250/341, 339, 339, 358.1; 356/445, 447, 446, 41

[56] References Cited

U.S. PATENT DOCUMENTS

| | | | |
|---|---|---|---|
| 3,776,642 | 12/1973 | Anson et al. | 356/188 |
| 3,877,818 | 4/1975 | Button et al. | 356/445 |
| 4,286,327 | 8/1981 | Rosenthal et al. | 364/498 |
| 4,341,473 | 7/1982 | Mast | 356/446 |
| 4,515,165 | 5/1985 | Carrol | 250/341 |

OTHER PUBLICATIONS

"An Introduction to Near Infrared Quantitative Analysis," presented by Robert D. Rosenthal, at 1977 Annual Meeting of Amerian Association of Cereal Chemists.

Primary Examiner—Carolyn E. Fields
Assistant Examiner—Richard Hanig
Attorney, Agent, or Firm—Bernard, Rothwell & Brown

[57] ABSTRACT

A non-destructive testing instrument useful for measuring of organic constituents of materials utilizes interactance of near infrared radiation from near infrared emitting diodes positioned at one end of a light transmitting cylinder having a length sufficient so that diode point sources provide uniform radiation at the other end of the cylinder, the cylinder being shielded from light. A detector, which may be inside the cylinder, detects the interactance from such radiation to provide a measurement of body fat utilizing a unique formula and unique measuring technique to prevent noise and incorrect measurements.

28 Claims, 7 Drawing Figures

NEAR INFRARED APPARATUS FOR MEASUREMENT OF ORGANIC CONSTITUENTS OF MATERIAL

BACKGROUND OF THE INVENTION

1. Field of the Invention

This invention relates to improvements in instruments for performing near infrared quantitative analysis of organic constituents, such as fat/oil in living bodies as well as in other materials.

2. Prior Art

Two types of near infrared quantitative analysis instruments are known and commercially available. The first type analyzes near-IR energy reflected off the surface of a sample to provide quantitative data on the organic constituents that are present such as protein, oil, and moisture. These type instruments require the sample surface to be very consistent thereby necessitating that the sample be ground into a fine powder with consistent particle size. An example of this type of reflectance instrument is described by James H. Ansow (et al) in U.S. Pat. No. 3,776,642 "Grain Analysis Computer." For a general introduction to near infrared quantitative analysis, see the paper presented by Robert D. Rosenthal to the 1977 annual meeting of American Association of Cereal Chemists entitled "An Introduction to Near Infrared Quantitative Analysis."

A second type of near infrared quantitative instrument analyzes the energy transmitted through a finite thickness of sample (e.g., 2 cm) to provide quantitative data on the amounts of organic constituents present. An example of an instrument of this type is described in U.S. Pat. No. 4,286,327 granted Aug. 25, 1981 to Robert D. Rosenthal and Scott Rosenthal, entitled "Apparatus for Near Infrared Quantitative Analysis" and assigned to the assignee of this invention. This type of transmission measurement approach avoids the requirement that samples be ground into a uniform particle size powder (as in the previous described reflectance measurement approach). However, the transmission approach requires that access to the sample be available on two opposite surfaces; the surface where near infrared energy enters the sample, and the opposite surface where energy exits from the sample.

In certain applications, neither the reflectance measurement need for grinding the sample into a uniform powder, nor the transmission need for a two-sided measurement, can be accomplished. One example of this type of difficult application is the desire to measure the amount of oil in sunflower seeds. Sunflower seeds are highly opaque and thus extremely difficult to measure using transmission technique. It is also extremely difficult to measure reflectance using sunflower seeds because their high oil content, coupled with their tough hull (i.e., shell), precludes grinding them into a fine powder with uniform particle size.

Another example of a difficult application is the desire to measure the amount of fat in humans and in animals.

Fat testing has many uses, but one of the most promising is in connection with non-destructive body fat testing used for medical purposes. The percentage of body fat is an important piece of medical information, and if inexpensive and accurate body fat testing instruments were available, it is believed that most physicians would have one in their offices. It is also believed that many hospitals, sports teams and individual athletes would also have them. Information as to the percentage of body fat could be quite useful in medical diagnosis, medical treatments and general monitoring of a human body's condition, not unlike the uses of blood pressure measuring instruments.

At present there are a number of different ways of measuring human body fat. Obviously, when testing on humans, a non-destructive and non-invasive test or procedure is highly desirable. The most accurate (but also the most frightening) test is a bouyancy test. In such tests a human is weighed out of water and then is weighed in water. However, to be weighed in water all air must be out of the subject's lungs. Obviously such tests require at the very minimum a pool of water and underwater scales, something not available in every physician's office. It is also quite frightening to the test subject who thinks he may drown.

The most common presently known way of measuring body fat is to caliper a pinch of body fat at four separate places on the body, add the total measurement in millimeters and divide by two to get a percentage of body fat. Although this is the most common method in use, it is probably the least accurate. While it is simple and all that is required is a pair of calipers and the ability to add and divide, it is not particularly speedy and its most serious drawback is the lack of accuracy.

Another means of measuring the percentage of body fat is to inject deuterium oxide ($D_2O$), then draw blood one hour later and analyze the blood. This method also has its disadvantages in that most people do not like to be injected with anything and this method is not widely used.

The United States Department of Agriculture is interested in the determination of body fat and has experimented in connection with the use of near infrared radiation technology utilizing an optical interactive system with fiber optic tubes. This U.S.D.A. method of testing currently shows the most promise of all of the known approaches to body fat testing.

The U.S.D.A. testing procedure utilizes near infrared radiation and an optical interactance principle in which instead of utilizing reflectance, transmission or a combination of reflectance and transmission, a source of light is directed into the body fat mass by means of a plurality of optical fibers arranged in a circular pattern and a detector is positioned at the end of a second fiber optic bundle located in the center of the illumination tube with an opaque mask separating the illuminating fiber optic tube from the detecting fiber optic bundle on the surface of the body fat between them. The interactance of the light with the body fat is detected by the detector and utilized for a reading.

While the U.S.D.A. instrument shows promise, especially from the standpoint of providing accurate and versatile measurements, it is expensive to manufacture utilizing expensive fiber optics. An article describing the U.S.D.A. development is currently being prepared for publication.

SUMMARY OF THIS INVENTION

This invention utilizes the principle of infrared radiation interactance with multiple selected wavelength infrared emitting diodes (IREDs) providing the source of optical radiation through a translucent cylinder (tube), acting as a light pipe, formed of a material that does not unduly absorb the infrared energy in the bandwidth of interest, i.e., the spectral absorption curve is reasonably flat in the bandwidth of interest. In one embodiment, two pairs of two IREDs are equally spaced around the periphery of one end of the tube and the tube is of sufficient length with sufficient internal light-scattering to smooth out the pulsed light sources and provide a uniform circular torus of infrared radiation at the end of the tube that touches the test subject. In another embodiment, three pairs of IREDs are equally spaced around the tube. The infrared radiation goes into the test subject, and via interactance, a portion of the energy is re-emitted from the subject in the center of the tube and detected on a silicon detector which is located behind an optically transparent, but electrically conductive window. An inexpensive amplifier is positioned within the tube which feeds a read-out box. The use of unique measuring and calculating techniques overcome the problems of accuracy due to color of the skin and pressure of the instrument on the skin. Multiple integrated readings of each IRED are taken to lower the measurement noise and the first group of readings are compared to the next group's readings to see if they are within tolerance and if not, it means the probe has moved and the measurement is in error and needs to be retaken.

DETAILED DESCRIPTION OF THE PREFERRED EMBODIMENTS

Figure 1:
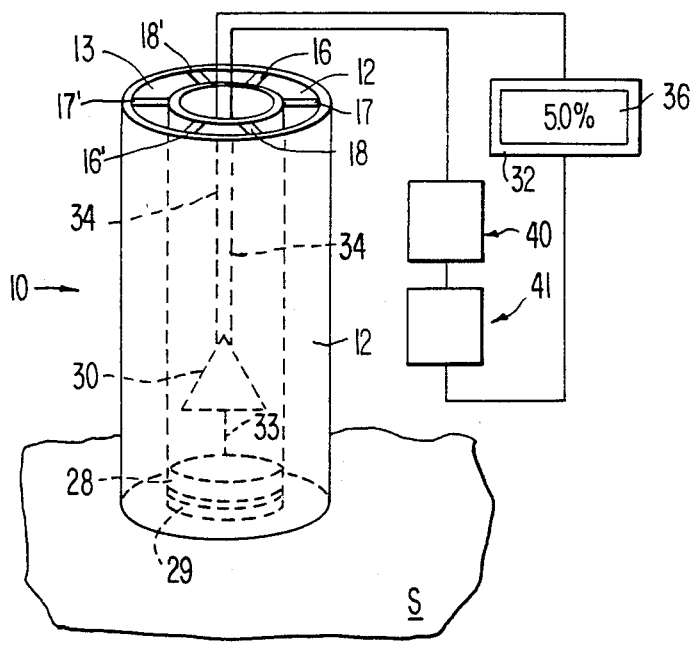
FIG. 1 is a partially schematic perspective view of the instrument of this invention.
Figure 7:
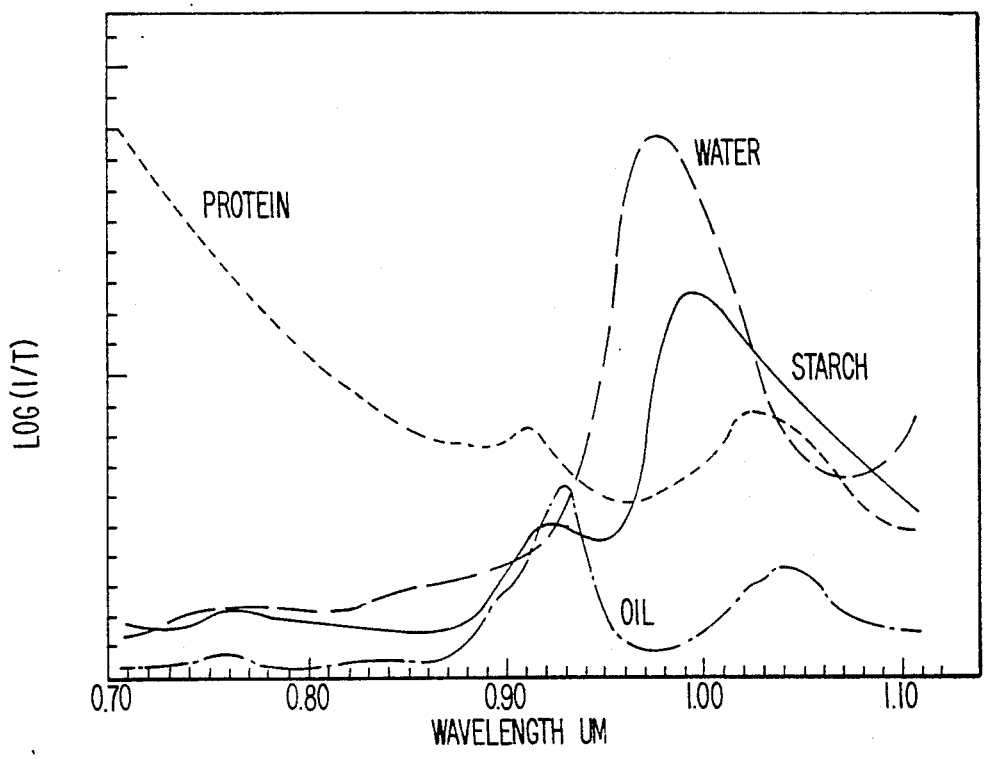
FIG. 7 is a graphic depiction of near infrared absorption spectrum.

With reference to FIG. 1, the instrument 10 is of hollow cylindrical form and includes a hollow tubular member 12 having a wall of solid translucent material selected so that it transmits and does not substantially or inconsistently absorb near infrared energy in the bandwidth of interest, namely, from about 800 to about 1100 nanometers (FIG. 7). Examples of suitable materials out of which tubular member 12 may be constructed include, but are not limited to, translucent nylon, translucent polytetrafluoroethylene and the like.

Means for providing at least one point source of near infrared radiation of a predetermined wavelength is positioned at an upper end portion 13 of tubular member 12. The near infrared point source means at the upper end portion 13 of tube 12 are positioned so that near infrared radiation of a predetermined wavelength or wavelengths emitting from the point source means will be transmitted by the tubular member 12 from the upper end portion 13 to a flat bottom surface 14 of tube 12. The near infrared point source means preferably comprises a plurality of pairs of two infrared emitting diodes (IREDs). The IREDs are preferably positioned symmetrically about the upper end part 13 of tube 12, with the two IREDs which comprise a pair of IREDs being of about the same wavelength and being peripherally positioned approximately 180° apart around the upper end of tube 12. Three pairs of such IREDs, 16, 16', 17, 17', 18 and 18', are shown in a preferred embodiment illustrated in FIG. 1. In other exemplary embodiments, two or four pairs of IREDs are utilized as the point source means.

Light transmitting tube 12 is of a suitable length to provide sufficient internal light scattering to smooth out the pulsed light sources so that light from the IREDs is transmitted through tube 12 and emerges uniformly at the bottom surface 14 of the tube. For example, a suitable length for a 1 inch diameter extruded translucent nylon tube, having a wall thickness of ⅛ inch, is about 1 ¾ inch.

Preferably, the tube 12 is no longer than is necessary to uniformly smooth out the pulsed light sources, in order to minimize the loss of near infrared radiation. The ideal tube length can be easily determined by utilizing a commercially available infrared viewer (nightscope). A tube may be sized by observing near infrared radiation passing through the tube and trimming the tube until the light emerges uniformly. A silicon detector is then passed around the end of the tube to check for uniform output.

For light shielding purposes, the cylindrical walls of tubular light transmitting member 12 are shielded on the outside by an outer tubular opaque shield 20 and on the inside by inner tubular opaque shield 22. The upper end portion 13 of tubular member 12 is also shielded from ambient light by a top cover, not shown.

Figure 2:
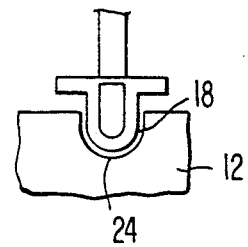
FIG. 2 is a detailed sectional partially schematic view of a portion of the instrument of this invention.

In a preferred embodiment illustrated in FIG. 1, infrared emitting diodes 16, 16', 17, 17', 18 and 18' are spaced 60° apart with similar wavelength infrared emitting diodes spaced 180° apart and positioned in notches 24 in the top surface of the upper end portion 13 of light-transmitting tube 12 as shown in FIG. 2. Two of the three near infrared emitting diode pairs are selected within manufacturing tolerance to emit radiation with a peak wavelength between 930 and 950 nanometers spaced 5 to 15 nanometers apart, thus corresponding to the oil/fat absorption shown in FIG. 7. The third pair of infrared emitting diodes are selected to emit radiation with a peak wavelength between 880 and 890 nanometers.

Figure 3:
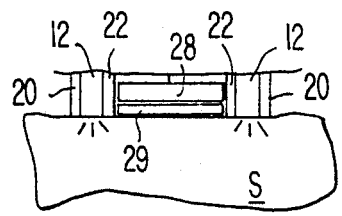
FIG. 3 is a detailed sectional partially schematic elevation view of the lower end of the instrument of this invention.

An optical detector 28, capable of detecting near infrared radiation, is positioned inside of and at the bottom end portion of the tubular member 12 as shown in FIGS. 1 and 3. Inner tubular shield 22 is positioned between detector 28 and transmitting tube 12, thereby providing an opaque mask which prevents near infrared radiation from tube 12 from impinging directly on detector 28. Optical detector 28 generates an electrical signal when the detector detects light.

The optical detector 28 is connected to the input of an electrical signal amplifier 30 by suitable electrical conducting means 33. Amplifier 30 may be an inexpensive signal amplifier, and amplifies signals generated by detector 28 in response to light detected by the detector. The detector 28 preferably is positioned within tube 22. The output of amplifier 30 feeds the amplified signal generated by detector 28 to a readout box 32 through conductive lines 34. The readout box 32 may have a display 36 for directly reading the percentage of fat in a test subject S.

An electrically conductive window 29, which is transparent to near infrared energy, is grounded directly to the apparatus electronics. Window 29 is located in front of the optical detector 28. This conductive window provides shielding from electro-magnetic interferences that are commonly encountered in industrial and consumer premises.

This invention utilizes the principle of interactance, which principle is known in the art and differs from reflectance and transmittance. In interactance, light from a source is shielded by an opaque member from a detector and interactance of the light with the test subject is then detected by the detector.

The U.S.D.A. publications for measuring body fat utilize the formula $\Delta O.D. = O.D._B - O.D._A$ where O.D. is optical density and is equal to log of one over interactance and $O.D._B$ and $O.D._A$ are between 930 and 950 nanometers spaced 5 to 15 nanometers apart with $O.D._B$ being the longer wavelength.

The present invention modifies that formula as $$\Delta O.D. = \frac{O.D._B - O.D._A}{O.D._B + O.D._A} + O.D._C \text{ or}$$

$$\frac{O.D._B - O.D._A}{O.D._A} + O.D._C \text{ or}$$

$$\frac{O.D._B - O.D._A}{O.D._B} + O.D._C \text{ or } \frac{O.D._A - O.D._B}{O.D._B - O.D._C}$$

where $O.D._C$ is the optical density between 880 and 890 nanometers. Using this formula overcomes the problem of incorrect reading due to color of the skin.

In operation, the bottom surface 14 and window 29 are positioned against a surface of test subject S. Light emerging from end 14 interacts with test subject S and is detected by detector 28. Detector 28 then generates an electrical signal which is processed as described above.

Additionally, this invention provides for multiple readings of each IRED to lower the noise utilizing data processing means. Multiple readings of each IRED is accomplished by feeding the output of amplifier 33 to an integrating analog-to-digital converter 40 having a twelve bit output, which is connected to a digital processor 41 connected to readout box 32.

Figure 4:
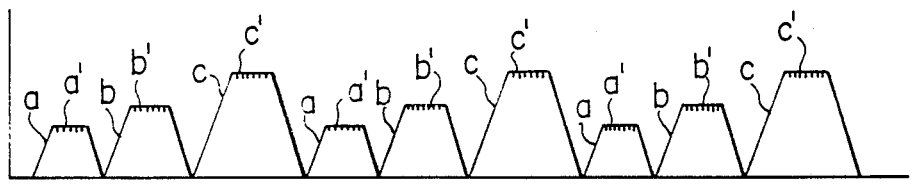
FIG. 4 is a waveform illustrating taking of measurements in accordance with this invention.

FIG. 4 is an illustration of three cycles of the output and reading of the IRED. Within the top of each waveform, such as waveform a, there are multiple integrated and separate readings taken as illustrated schematically at a'. Similarly, for waveform b and c there are also multiple integrated measurements taken at the top of the waveform. Similar readings are taken for each of the waveforms a, b and c through several cycles (three cycles are illustrated in FIG. 4). The integrated multiple readings of a and a' of the first measurement are compared to the integrated multiple readings of a and a' of the second multiple integrated readings of a and a' of the third to see if they are within a preset tolerance. If not, it means the instrument 10 has moved and the measurement will need to be aborted as it will not give an accurate reading when the instrument is moved.

The invention is particularly useful for measuring percent body fat as indicated above, but is not limited to such. An instrument according to this invention may be utilized to measure organic constituents such as starch, sugar, fiber, possibly protein and even moisture content. It can also measure the maturity of avocados and measure the ripeness or maturity of other fruits, such as, e.g., apples and peaches. However, IREDs that provide different wavelengths are used for these measurements (see FIG. 7).

Figure 6:
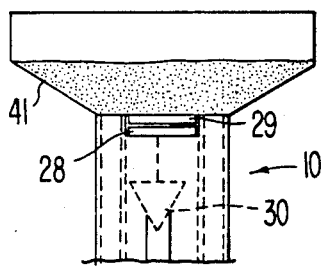
FIG. 6 is cross-section partially schematic view of the probe of this invention in a configuration to measure powders.

An alternative embodiment of the invention, illustrated in FIG. 6, is useful in measuring fat/oil or other organic constituents in powdered or particulate type materials such as ground sunflower seeds. The sunflower seeds are ground for a few seconds in a low cost, coffee type grinder with a knife type blade (not shown). This type of grinder breaks the seeds into non-uniform particles which are not suitable for reflectance measurements but are acceptable for interactance measurement. The ground seeds are spooned into a funnel 41 that is attached to the probe of FIG. 1 which is looking upward. The measurement is otherwise performed as previously described.

Figure 5:
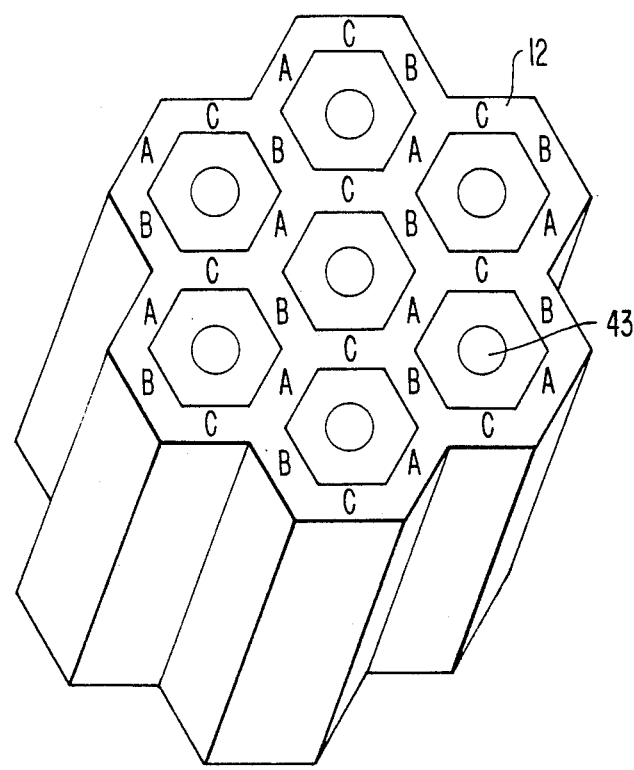
FIG. 5 is a partially schematic perspective view of an alternate measurement probe of this invention.

A further variation of the invention, FIG. 5, uses a cluster of hexagon cylinders to allow illuminating larger samples that may have inconsistent constituent distribution. One example of such a product is ground beef, particularly if the beef has only been ground once. Separate pairs of IREDs are positioned about each hexagon. In this case, all "A" IREDs are energized then shut off; then all "B" IREDs, then all "C" IREDs. A separate detector can be used in the center of each hexagon, with the output of all detectors summed. However, an advantageously inexpensive embodiment utilizes a low cost transparent light pipe 43 (e.g., clear acrylic rod) in the center of all hexagons leading back to a single photodetector.

An example of one embodiment of the invention utilizes copper tubing of the type normally used in plumbing as the external tubular opaque shield 20 of the probe, with a $1\frac{3}{4}''$ long transmitting tubular member 12 constructed of 1" diameter translucent nylon tube having a $\frac{1}{8}''$ wall thickness. The IREDs used are type CYW-13 manufactured by Telefunken and normally used for remote control of television sets. These IREDs were sorted for specific wavelengths using a modified Cary-14 Spectrophotometer. The amplifier used is an RCA 3160 used in a conventional inverting gain circuit with DC bias adjustment. The near infrared transparent, electrically conducting window is made from wire-reinforced PVC glazing sheet (Trade name: "Realitz"). The system operation is accomplished using a modified Trebor T-10 single board computer with an Intel 8085 microprocessor. The displays are Fairchild 7 segment LED type FND-560.

It can be seen that this invention provides a unique, inexpensive and reliable instrument for measuring body fat, and the fat/oil content of non-uniform powders and the like, in a non-destructive manner using near infrared radiation.

What is claimed is:

1. A near infrared quantitative instrument for measuring a fat/oil-containing sample material, comprising:
    (a) means for providing at least one point source of near infrared radiation;
    (b) a tube having a wall portion, the wall portion comprising a material which is capable of transmitting near infrared radiation; the material having a composition which does not substantially or inconsistently absorb near infrared radiation, the tube having first and second ends, the point source means being positioned at the first end of said tube for transmitting near infrared radiation through the wall portion of said tube, the tube being of a sufficient length that near infrared radiation from point source means positioned at the first end of the tube will emerge substantially uniform at the second end of the tube; the second end of the tube for positioning against the said sample material; the second end of the tube peripherally defining a generally central area;

(c) a near infrared radiation detector positioned for detecting near infrared radiation entering the generally central area peripherally defined by the second end of the tube, the detector being capable of providing an electrical signal upon detection of near infrared radiation;

(d) means for preventing near infrared radiation from the wall of the tube from impinging directly on said detector;

(e) means for shielding the outside of the tube from ambient light;

(f) means connected to the detector for amplifying an electrical signal provided by said detector; and (g) means for data processing and readout, the data processing and readout means being connected to the amplifier means and being capable of processing the amplified signal and providing a readout indicative of the percent fat in the sample material.

2. The measuring instrument of claim 1 further including an electro-magnetic interference shield comprising a grounded electrically conductive window which is substantially transparent to near infrared energy, the window being positioned at the second end of the tube and shielding the detector from electro-magnetic interference.

3. The measuring instrument of claim 2 wherein the detector is positioned inside the tube near the second end thereof and adjacent the window.

4. The measuring instrument of claim 1 including a plurality of said tubes arranged in a group.

5. The measuring instrument of claim 2 including a plurality of said tubes arranged in a group.

6. The measuring instrument of claim 3 including a plurality of said tubes arranged in a group.

7. The instrument of claim 1 wherein the tube is a hollow cylinder.

8. The instrument of claim 2 wherein the tube is a hollow cylinder.

9. The instrument of claim 3 wherein the tube is a hollow cylinder.

10. The instrument of claim 7 wherein the point source means comprises a plurality of pairs of two infrared emitting diodes, the diodes being peripherally positioned generally symmetrically around the cylinder, the two diodes comprising a pair of diodes being of about the same wavelength, wherein two diodes comprising a pair of diodes of about the same wavelength are peripherally positioned about, 180° apart around the cylinder.

11. The instrument of claim 8 wherein the point source means comprises a plurality of pairs of two infrared emitting diodes, the diodes being peripherally positioned generally symmetrically around the cylinder, the two diodes comprising a pair of diodes being of about the same wavelength, wherein two diodes comprising a pair of diodes of about the same wavelength are peripherally positioned about 180° apart around the cylinder.

12. The instrument of claim 9 wherein the point source means comprises a plurality of pairs of two infrared emitting diodes, the diodes being peripherally positioned generally symmetrically around the cylinder, the two diodes comprising a pair of diodes being of about the same wavelength, wherein two diodes comprising a pair of diodes of about the same wavelength are peripherally positioned about 180° apart around the cylinder.

13. The instrument of claim 10 comprising three pairs of said diodes.

14. The instrument of claim 11 comprising three pairs of said diodes.

15. The instrument of claim 12 comprising three pairs of said diodes.

16. The instrument of claim 13 for fat/oil measurement wherein two of the pairs of infrared emitting diodes are selected to produce, within manufacturing tolerance, a peak wavelength between 930 and 950 nanometers spaced between 5 and 15 nanometers apart, and the third pair with a peak wavelength between 880 and 890 nanometers.

17. The instrument of claim 14 for fat/oil measurement wherein two of the pairs of infrared emitting diodes are selected to produce, within manufacturing tolerance, a peak wavelength between 930 and 950 nanometers spaced between 5 and 15 nanometers apart, and the third pair with a peak wavelength between 880 and 890 nanometers.

18. The instrument of claim 15 for fat/oil measurement wherein two of the pairs of infrared emitting diodes are selected to produce, within manufacturing tolerance, a peak wavelength between 930 and 950 nanometers spaced between 5 and 15 nanometers apart, and the third pair with a peak wavelength between 880 and 890 nanometers.

19. The instrument of claim 2 wherein the material of the cylinder wall is polytetrafluoroethylene or nylon.

20. The instrument of claim 2 wherein the amplifying means is completely contained within the cylinder.

21. The instrument of claim 6 wherein the data processing means compares a plurality of simultaneous readings to see if successive readings are within a predetermined tolerance.

22. The instrument of claim 4 wherein the point source means comprises infrared emitting diodes, the diodes being peripherally positioned about the first end of each tube so that about the periphery of each tube is located a plurality of pairs of two diodes, the diodes positioned about each tube being positioned generally symmetrically, the two diodes comprising a pair of diodes being of about the same wavelength, wherein two diodes comprising a pair of diodes of about the same wavelength are positioned about 180° apart about a tube.

23. The instrument of claim 12 further including a funnel member peripherally attached about the second end of the tube for holding ground, powdered or particulate sample material adjacent said window.

24. The instrument of claim 22 comprising two, three or four pairs of said diodes.

25. The instrument of claim 22 comprising three pairs of said diodes.

26. The instrument of claim 10 comprising two or four pairs of said diodes.

27. The instrument of claim 11 comprising two or four pairs of said diodes.

28. The instrument of claim 12 comprising two or four pairs of said diodes.

* * * * *